(12) United States Patent
Yan et al.

(10) Patent No.: US 10,883,927 B2
(45) Date of Patent: Jan. 5, 2021

(54) HEMOGLOBIN DETECTING DEVICE

(71) Applicant: Redeye Inc., Hsinchu (TW)

(72) Inventors: Shuo-Ting Yan, Hsinchu (TW); I-Hua Wang, Hsinchu (TW)

(73) Assignee: Taiwan Redeye Biomedical Inc., Hsinchu (TW)

( * ) Notice: Subject to any disclaimer, the term of this patent is extended or adjusted under 35 U.S.C. 154(b) by 29 days.

(21) Appl. No.: 16/432,459

(22) Filed: Jun. 5, 2019

(65) Prior Publication Data
US 2020/0386673 A1 Dec. 10, 2020

(51) Int. Cl.
*G01N 21/31* (2006.01)
*G01N 33/49* (2006.01)
(Continued)

(52) U.S. Cl.
CPC .......... *G01N 21/31* (2013.01); *G01J 3/0256* (2013.01); *G01J 3/0272* (2013.01); *G01J 3/0291* (2013.01);
(Continued)

(58) Field of Classification Search
CPC ...... G01N 21/01; G01N 21/25; G01N 21/251; G01N 21/255; G01N 21/27; G01N 21/31; G01N 21/3103; G01N 21/314; G01N 21/3151; G01N 21/59; G01N 21/62; G01N 21/63; G01N 21/64; G01N 21/65; G01N 2021/3125; G01N 2021/3129; G01N 2021/3133; G01N 2021/3144; G01N 2021/0106; G01N 2021/0112; G01N 2021/0118; G01N 2021/0125; G01N 2021/0131; G01N 2021/0137; G01N 2021/0143; G01N 33/48; G01N 33/483; G01N 33/4833; G01N 33/487; G01N 33/48707; G01N 33/48785; G01N 33/49; G01N 33/493; G01J 1/02; G01J 1/0204;
(Continued)

(56) References Cited

U.S. PATENT DOCUMENTS 4,997,769 A * 3/1991 Lundsgaard ........... G01N 21/31
436/66
6,262,798 B1 * 7/2001 Shepherd ............... G01N 21/31
356/39

(Continued)

*Primary Examiner* — Gordon J Stock, Jr.
(74) *Attorney, Agent, or Firm* — Thomas J. Nikolai; DeWitt LLP

(57) ABSTRACT

A hemoglobin detecting device includes a shell component connected with a fixing part that engages with an outer side of a smart device. A processor unit, a light source, a light detection module and a transmission unit are mounted inside the shell component. The light source generates a first light beam, and the light detection module receives a second light beam that is generated when the first light beam travels through an analyte solution and is reflected. The processor unit determines whether the absorption spectrum of the analyte solution matches a target spectrum, and generates a result information according to the detection. The transmission unit transmits the result information to the smart device and displays an indication of the result. The hemoglobin detecting device provides a fast and accurate way to detect blood in a stool solution, and can be applied to and cooperate with all kinds of smart devices.

16 Claims, 16 Drawing Sheets

(51) Int. Cl.
  *G01N 33/483* (2006.01)
  *G01N 33/487* (2006.01)
  *G01N 21/27* (2006.01)
  *G01J 3/02* (2006.01)

(52) U.S. Cl.
  CPC ........... *G01N 21/27* (2013.01); *G01N 21/314* (2013.01); *G01N 33/487* (2013.01); *G01N 33/4833* (2013.01); *G01N 33/49* (2013.01); *G01N 2201/068* (2013.01)

(58) Field of Classification Search
  CPC ...... G01J 1/0209; G01J 1/0233; G01J 1/0271; G01J 1/04; G01J 1/0403; G01J 2001/0257; G01J 2001/0261; G01J 3/02; G01J 3/0202; G01J 3/0256; G01J 3/0259; G01J 3/0272; G01J 3/0291; A61B 10/0038
  USPC .......................................................... 356/39
  See application file for complete search history.

(56) References Cited

U.S. PATENT DOCUMENTS

| | | | | |
|---|---|---|---|---|
| 6,975,395 B1* | 12/2005 | Gentieu | ................ | G01J 3/02 356/326 |
| 8,305,577 B2* | 11/2012 | Kivioja | ................ | G01J 3/0291 356/328 |
| 8,483,789 B2* | 7/2013 | Higgins | ................ | A61B 5/0075 600/328 |
| 9,185,200 B2* | 11/2015 | Cunningham | .... | H04M 1/72527 |
| 9,271,099 B1* | 2/2016 | Sun | ................ | A61B 5/0402 |
| 9,339,234 B2* | 5/2016 | Chen | ................ | A61B 5/150358 |
| 9,772,227 B2* | 9/2017 | Scott | ................ | G01J 3/42 |
| 10,455,072 B2* | 10/2019 | Oppenheim | ........ | H04M 1/7253 |
| 2005/0261605 A1* | 11/2005 | Shemer | ................ | G01N 21/31 600/573 |
| 2006/0222567 A1* | 10/2006 | Kloepfer | ................ | G01N 33/558 422/68.1 |
| 2012/0052910 A1* | 3/2012 | Mu | ................ | H04M 1/72527 455/558 |
| 2014/0038222 A1* | 2/2014 | Alt | ................ | G01N 21/648 435/29 |
| 2015/0036139 A1* | 2/2015 | Hsu | ................ | G06F 1/1632 356/402 |
| 2016/0231171 A1* | 8/2016 | Assefa | ................ | G01J 3/0272 |
| 2016/0265974 A1* | 9/2016 | Ertel | ................ | G01J 3/0291 |
| 2017/0023542 A1* | 1/2017 | Wang | ................ | A61B 10/0064 |
| 2017/0212039 A1* | 7/2017 | Yan | ................ | G01J 3/10 |
| 2017/0303901 A1* | 10/2017 | Sekine | ................ | G01N 33/4833 |
| 2018/0120155 A1* | 5/2018 | Rosen | ................ | G01J 3/0272 |
| 2020/0025611 A1* | 1/2020 | Mai | ................ | G01J 3/0264 |
| 2020/0355702 A1* | 11/2020 | Yan | ................ | G01N 21/31 |

* cited by examiner

HEMOGLOBIN DETECTING DEVICE

BACKGROUND OF THE INVENTION

1. Field of the Invention

The present invention relates to a detecting device, particularly a hemoglobin detecting device.

2. Description of the Related Art

Hemoglobin exists in the blood of humans and most animals. When tissue inflammation, cancer tissue growth, or ulcers occur in internal organs, blood might leak from the damaged tissue, causing hemoglobin to appear in secretion such as stool, urine, saliva, or snivel. Therefore, detecting the hemoglobin in such secretion can be a crucial index for some specific lesions or diseases. For instance, stool occult blood test is an index for colorectal cancer, urine occult blood test is an index for bladder cancer, and sputum occult blood test is an index for bronchitis or lung cancer.

Among all cancers, colorectal cancer is one of the most commonly diagnosed cancers around the world. In the USA, 8% of the total cancer cases is colorectal cancer, which is ranked the $4^{th}$ among all cancers with a mortality rate ranked the second. China has 18.6% of the global colorectal cancer cases, with 20.1% of the mortalities in the world.

As stated above, one of the most commonly used indexes for colorectal cancer is the occult blood test. In other words, if blood or hemoglobin appears in the stool, it is likely that colorectal cancer or early stage symptom of such is appearing.

Nowadays, the most common solution for stool occult blood test is immunochemical fecal occult blood test (i-FOBT). In the procedure of i-FOBT, the subject is required to collect a sample of the fecal secretion, and send the sample back to the hospital by delivery or in person, so that the medical technologist can perform the occult blood test on the sample. However, such process needs long waiting time and leads to inconvenience, so normally the general public may only go through related physical examinations once a year or two. The inspection cycle is too long to discover the symptom as soon as it shows. On the other hand, blood tissue is not uniformly distributed in the stool, and the sample is only a small portion of the stool that may not include the part that contains blood, leading to a pseudo-negative result, which means the result of the occult blood test is negative, but a tumor or a polyp is already growing inside the intestine and causes bleeding. On the other hand, a tumor or a polyp may be bleeding intermittently instead of constantly. If the lesion did not bleed before or on the day the fecal sample is taken, the result of the occult blood test might also be pseudo-negative and leads to misdiagnosis.

In one of the related arts of remotely detecting stool or urine occult blood, a fluorescent agent or oxidant must be added into the toilet bowl before irradiating the solution in the toilet bowl with excitation light, and then detecting the photoluminescence from the solution to determine whether the secretion contains hemoglobin or blood. The operator must prepare the chemicals, leading to inconvenience.

In some other related art of remotely detecting stool or urine occult blood which also utilizes photoluminescence detection method, analyte such as stool or urine must be added into a reaction solution. The reaction solution includes multiple strong reducing agents that may cause burn when in contact with the skin.

In another related art, the operator of an occult blood test must collect the sample of the stool, and put it in the dilution liquid. After the testing process, the container must be cleaned with extra cleaning processes.

To sum up, among the related arts of secretion occult blood test, some require collected sample of stool or urine, while some require the use of additional chemicals for reaction such as fluorescent agent or reducing agent. Those procedures are complex and inconvenient, or even lead to potential danger, which may not be done frequently and may not be suitable for users to conduct at home.

SUMMARY OF THE INVENTION

An objective of the present invention is to provide a hemoglobin detecting device that cooperates with a smart device.

The hemoglobin detecting device includes a shell component, a fixing part, a processor unit, a transmission unit, a light source and a light detection module. The fixing part is connected to the shell component, so that the shell component can be engaged with a smart device. The light detection module is mounted inside the shell component, and the transmission unit, the light source, and the light detection module are electrically connected to the processor unit. The light source generates a first light beam, which passes through an analyte solution and is then reflected to form a second light beam. The light detection module receives the second light beam and generates a light intensity information.

The processor unit receives the light intensity information from the light detection module, and determines whether the absorption spectrum of the analyte solution matches a target spectrum. When the absorption spectrum of the analyte solution matches the target spectrum, the processor unit generates a positive result information; when the absorption spectrum of the analyte solution does not match the target spectrum, the processor unit generates a negative result information.

Furthermore, when the processor unit generates the positive result information or the negative result information, the transmission unit receives the positive result information or the negative result information, and transmits the positive result information or the negative result information to the smart device, with which the hemoglobin device is engaged.

The hemoglobin detecting device is designed to be engaged with a smart device such as a smart phone, a tablet computer, or a PDA, etc. The hemoglobin detecting device is electrically connected to the smart device through the transmission unit, so that the user can operate the detecting device and be informed of the result through the smart device. When the light source is turned on and points the light source to a container containing the analyte solution, the first light beam passes through the analyte solution, and the first light beam is reflected by a reflection surface of the container to form the second light beam.

The analyte solution is a liquid that includes human fecal extraction, for instance, the liquid solution in a toilet bowl that contains stool. When stool carrying blood tissue falls into the water in the toilet bowl, the blood in the stool will dissolve into the water around it. That is, if occult blood exists in the stool, the blood will also exist in the water in the toilet bowl, which is the analyte solution of the present invention. Furthermore, when the first light beam passes through the analyte solution, the first light beam will be partially absorbed by the analyte solution, and the second light beam, the reflected light beam of the first light beam, will contain information of the absorption spectrum of the analyte solution.

When the processor unit receives the light intensity information generated by the light detection module, the processor unit determines whether the absorption spectrum of the analyte solution matches the target spectrum. The target spectrum is the absorption spectrum of a blood solution. If the processor unit determines that the absorption spectrum of the analyte solution matches the target spectrum, it is confirmed that the analyte solution contains blood tissues, which indicates that the stool in the toilet bowl contains occult blood. Therefore the processor unit generates a positive result information. If the processor unit determines that the absorption spectrum of the analyte solution does not match the target spectrum, it is confirmed that the analyte solution does not contain blood tissue, which indicates that the stool in the toilet bowl does not contain occult blood. Therefore the processor unit generates a negative result information.

Since the hemoglobin detecting device of the present invention analyzes the absorption spectrum of the liquid containing the stool rather than testing the stool itself, it avoids the possibility of a pseudo-negative result caused by the collected sample not containing the part with blood, thus improving the reliability of the test results. In the process of detecting occult blood in stool using the hemoglobin detecting device, there is no sample collecting, no solution stirring, and no long waiting time for the result, thus enhancing the convenience of the whole process, with no consumable needed at all in the process. On the other hand, the device directly performs analyzation on the absorption spectrum of the solution itself by sending the first light beam and receiving the second light beam. So there is no need for adding any chemical agent such as fluorescent agent, reaction agent, or reductant, thereby eliminating the risks of user exposure to chemicals or environmental pollution.

The hemoglobin detecting device provides a convenient, fast and easy means to detect stool occult blood. The detecting device can be easily mounted onto a smart device and communicates with the smart device by either wireless connection or wired connection. The user can execute an application installed in the smart device to activate the detecting process. When the detecting device generates the result information of the detection, the user can be notified of the outcome instantly. The hemoglobin detecting device is applicable to any smart device with the application installed. Therefore, any ordinary user can perform self-examination for stool occult blood at home and obtain a result instantly, doing health management efficiently and independently.

Other objectives, advantages and novel features of the invention will become more apparent from the following detailed description when taken in conjunction with the accompanying drawings.

DETAILED DESCRIPTION OF THE INVENTION

Figure 1:
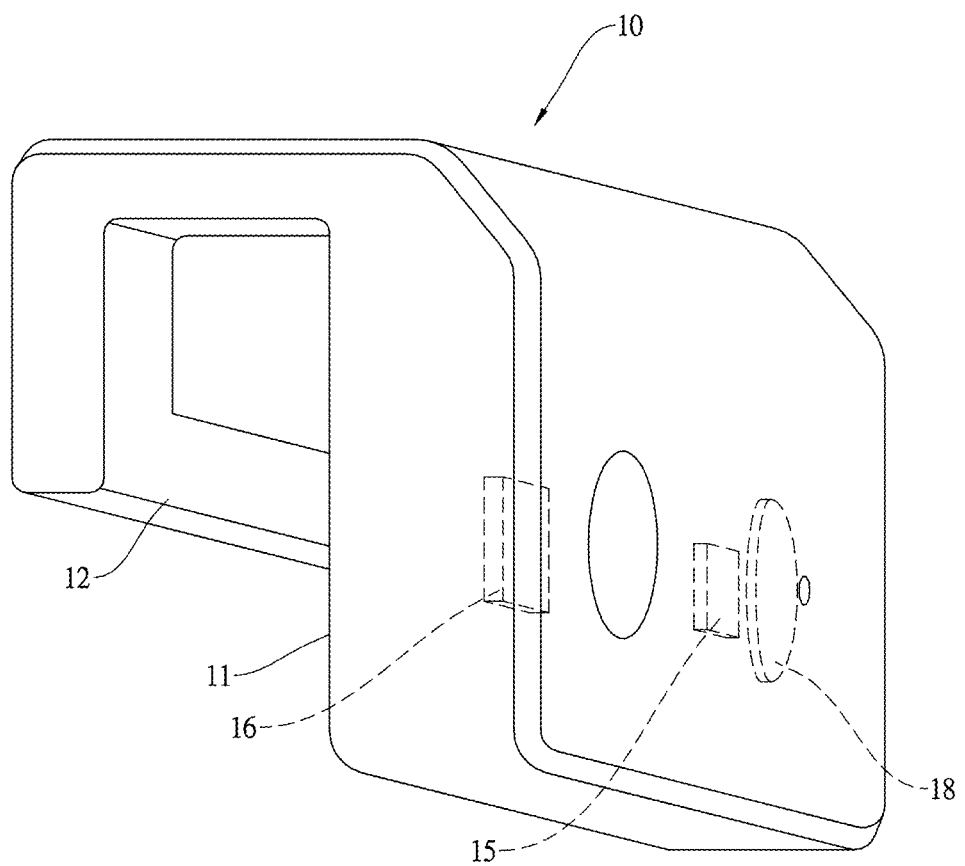
FIG. 1. is a perspective view of a first embodiment of a hemoglobin detecting device of the present invention.
Figure 2:
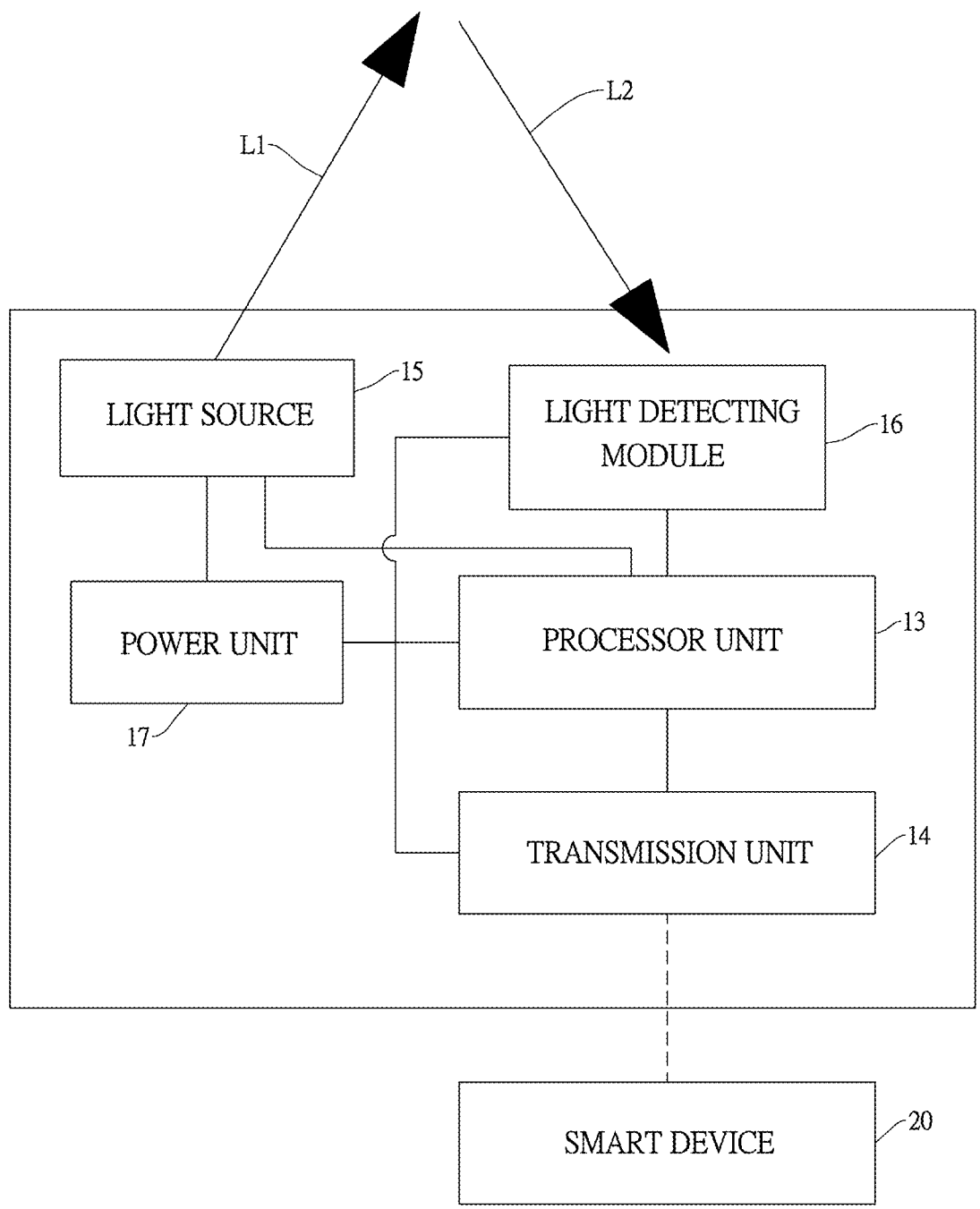
FIG. 2 is a block diagram of the hemoglobin detecting device of the present invention.
Figure 3:
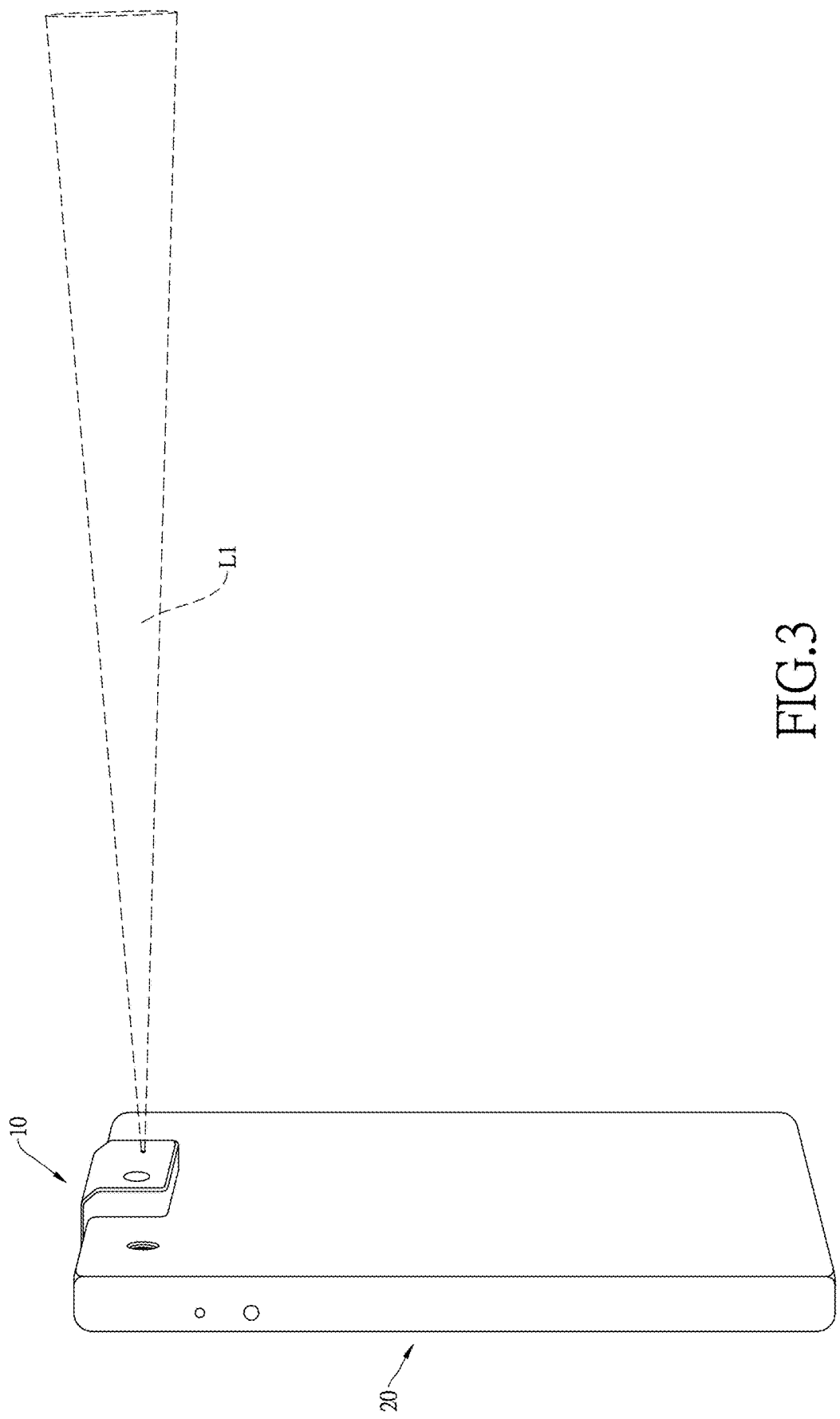
FIG. 3 is an operational perspective view of the hemoglobin detecting device of the present invention.

With reference to FIG. 1 to FIG. 3, the hemoglobin detecting device 10 includes a shell component 11, a fixing part 12, a processor unit 13, a transmission unit 14, a light source 15 and a light detection module 16. The fixing part 12 is connected to the shell component 11, so that the shell component 11 can be engaged with the outer side of a smart device 20. The light detection module 16 is mounted inside the shell component 11, while the transmission unit 14, the light source 15, and the light detection module 16 are electrically connected to the processor unit 13. The light source 15 generates a first light beam L1, which passes through an analyte solution and is then reflected to form a second light beam L2. The light detection module 16 receives the second light beam L2 and generates a light intensity information.

The processor unit 13 receives the light intensity information from the light detection module 16, and determines whether the absorption spectrum of the analyte solution matches a target spectrum. When the absorption spectrum of the analyte solution matches the target spectrum, the processor unit 13 generates a positive result information; when the absorption spectrum of the analyte solution does not match the target spectrum, the processor unit 13 generates a negative result information.

Furthermore, when the processor unit 13 generates the positive result information or the negative result information, the transmission unit 14 receives the positive result information or the negative result information and transmits the positive result information or the negative result information to the smart device 20, with which the hemoglobin device is engaged.

With reference to FIG. 2, the hemoglobin detecting device further includes a power unit 17. The power unit 17 is electrically connected to the processor unit 13, the transmission unit 14, the light source 15 and the light detection module 16 to provide electricity. The power unit 17 may be a lithium battery unit with DC/DC converter.

In a first embodiment of the present invention, the fixing part 12 and the outer wall of the shell component 11 form a C-shaped structure, and the width of the hollow part of the C-shaped structure fits a thickness or a width of the smart device 20. As a result, the user can mount the hemoglobin detecting device 10 onto the smart device 20 easily by pushing the C-shaped structure of the hemoglobin detecting device 10 onto the edge of the smart device 20 to engage with the smart device 20. In the present embodiment, when the hemoglobin detecting device 10 is mounted to the smart device 20, the light source 15 and the light detection module 16 are pointing toward the backside of the smart device 20, which is the opposite side of the display module of the smart device 20.

Figure 4:
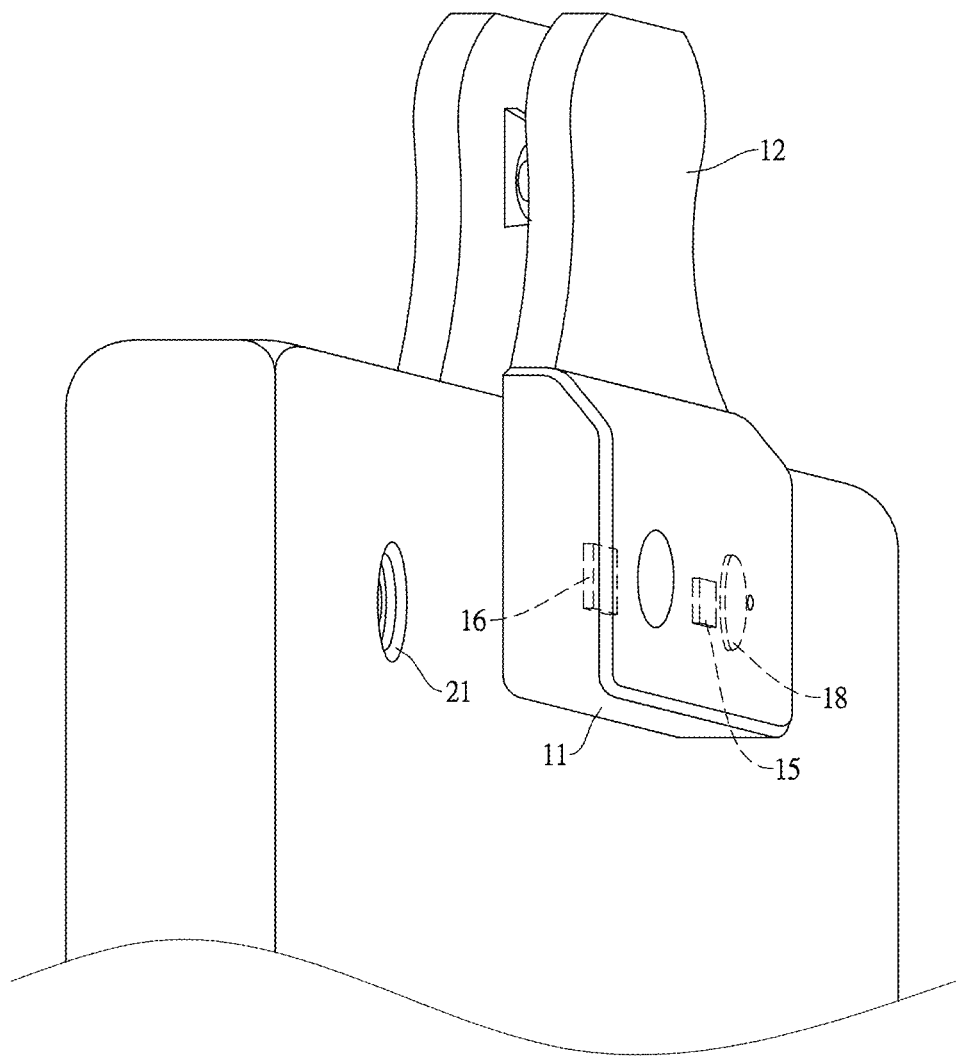
FIG. 4 is a perspective view of a second embodiment of the hemoglobin detecting device of the present invention.

With reference to FIG. 4, in a second embodiment of the present invention, the fixing part 12 is a clamping component. The clamping component includes two clamping arms, and the distance between the two clamping arms can be adjusted by hand. A user can mount the hemoglobin detecting device 10 onto the smart device 20 by clamping it to an edge of the smart device 20.

Figure 5:
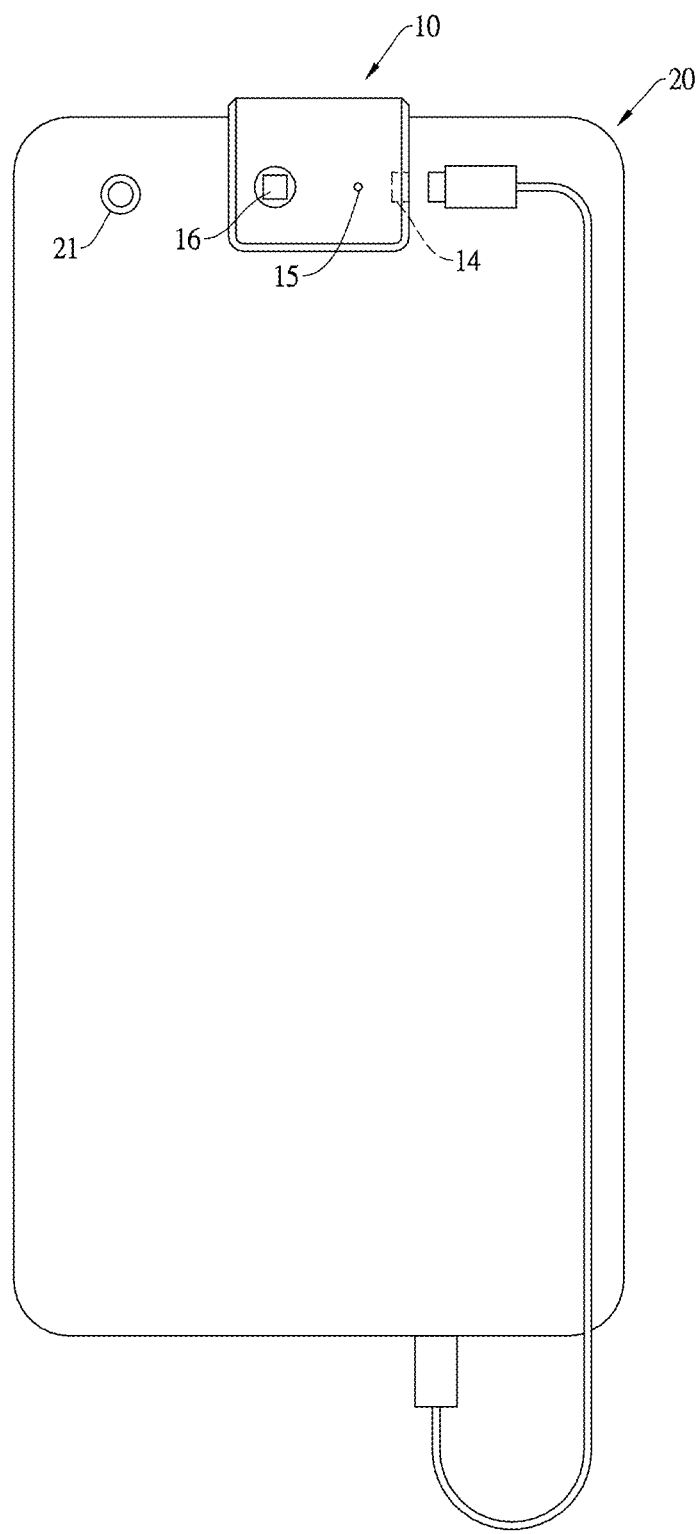
FIG. 5 is a schematic view of a third embodiment of the hemoglobin detecting device of the present invention.

With reference to FIG. 5, in a third embodiment, the transmission unit 14 is a female USB connecting port or a female lighting connecting port, and the transmission unit is connected to the corresponding connection port of the smart device through wire.

Figure 6:
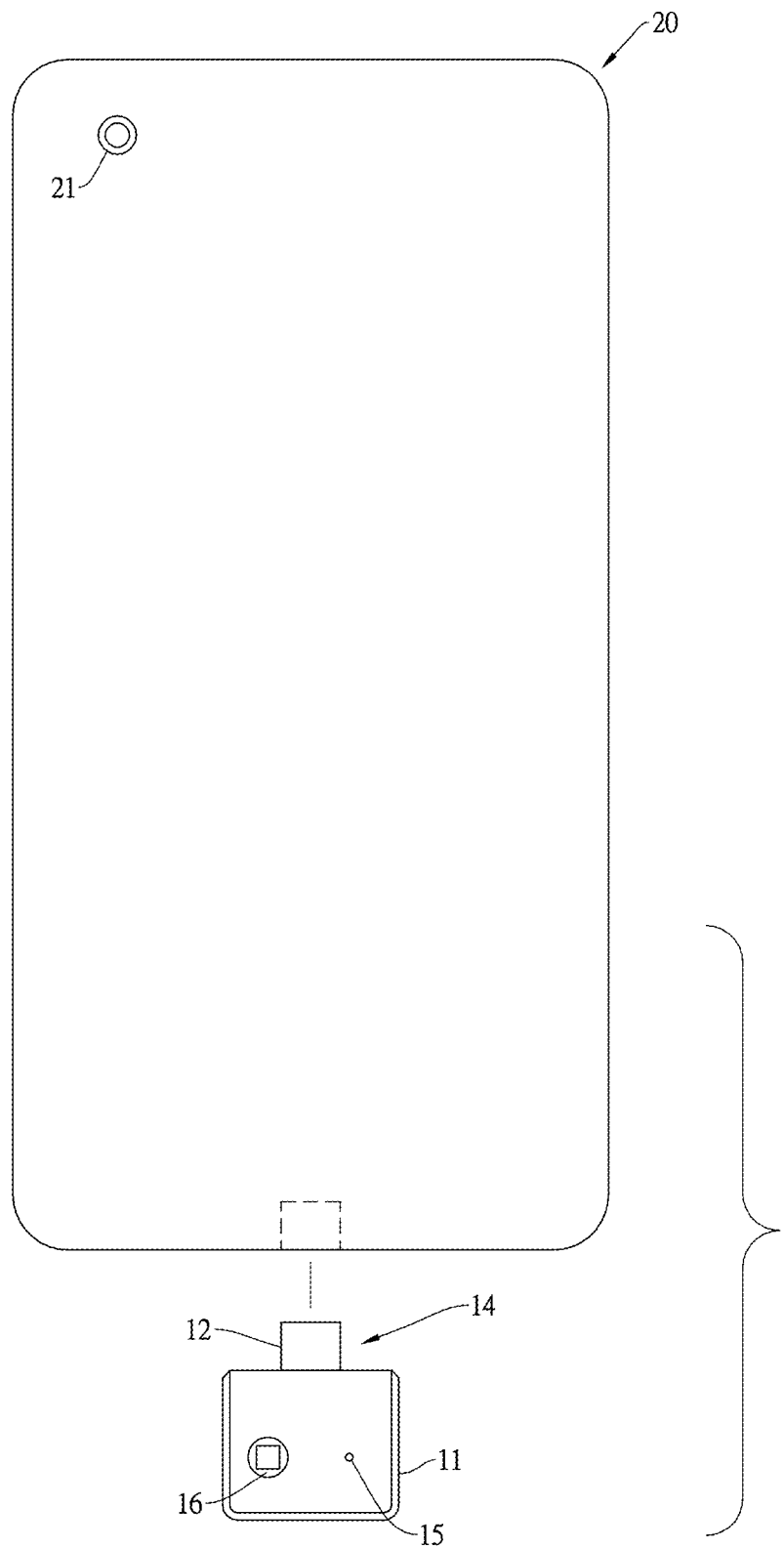
FIG. 6 is a schematic view of a fourth embodiment of the hemoglobin detecting device of the present invention.

With reference to FIG. 6, in a fourth embodiment of the present invention, the transmission unit 14 is a connection port, such as a male USB connecting port or a male lighting connecting port. The fixing part 12 is the engaging structure of the connecting port, such that the hemoglobin detecting device 10 is mounted and fixed on the smart device 20 when the connecting port is connected to the corresponding connecting port on the smart device 20. In the third and fourth embodiments, the power unit 17 may also be electrically connected to the transmission unit 14 and receives a power supplied from the smart device 20 through a power delivery protocol.

Figure 7:
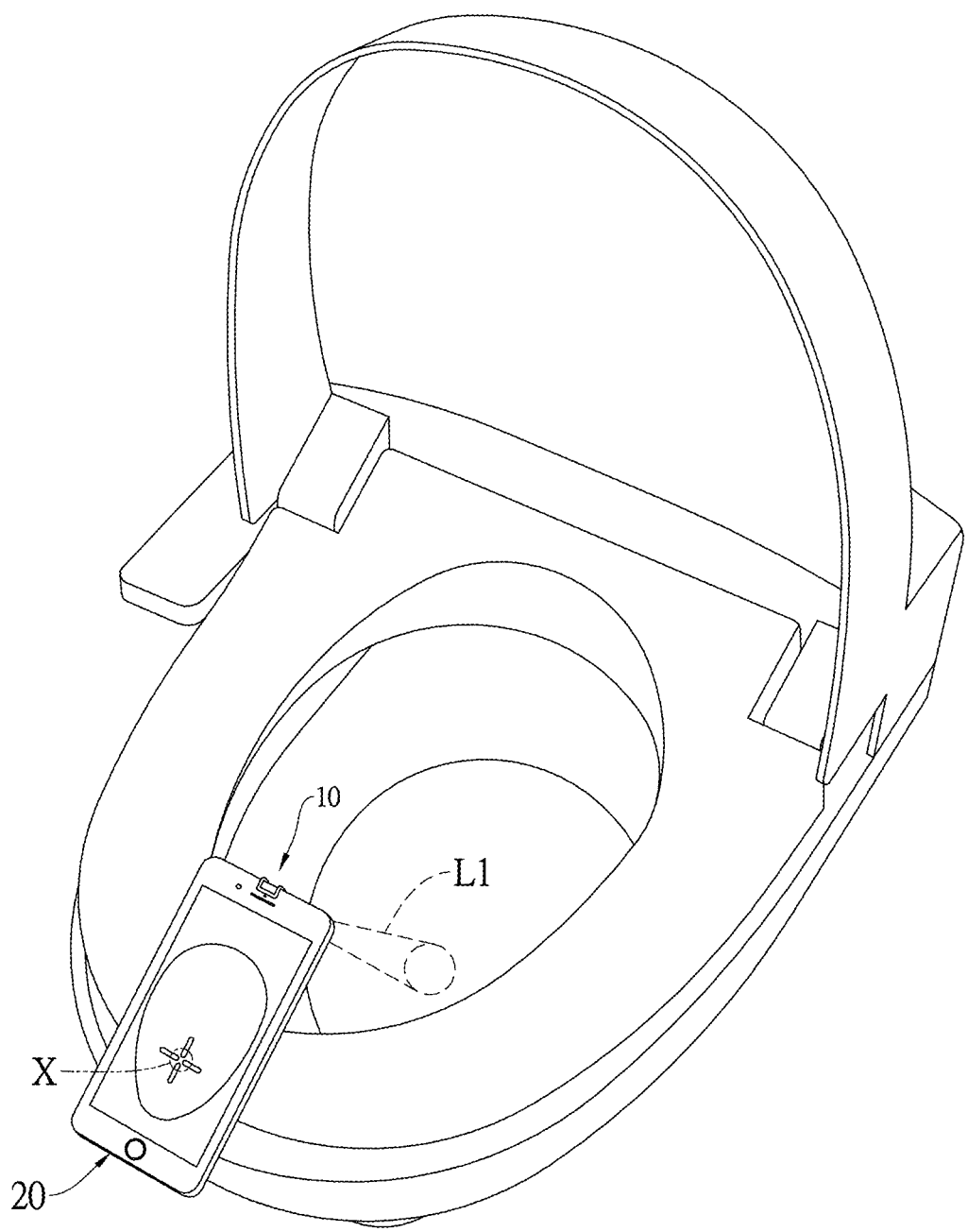
FIG. 7 is another operational perspective view of the hemoglobin detecting device of the present invention.

With reference to FIG. 2, in a fifth embodiment of the present invention, the transmission unit 14 of the hemoglobin detecting device 10 is wirelessly connected to the smart device 20, with which the hemoglobin detecting device 10 is engaged. The transmission unit 14 and the smart device 20 may be communicating through Bluetooth or Wi-Fi. The smart device 20 may be installed with an application, so that the user can operate and control the hemoglobin detecting device 10. For example, when the user presses a "start detecting" icon displayed on the smart device 20, the smart device 20 may send a first signal to the hemoglobin detecting device 10. When the hemoglobin detecting device 10 receives the first signal, the light source 15 begins to generate the first light beam L2, and the light detection module 16 begins to receive the second light beam L2. With reference to FIG. 7, furthermore, when the smart device 20 generates the first signal and the hemoglobin detecting device 10 begins the detecting, the application of the smart device 20 may execute an assisting program, and turns on the camera module 21 of the smart device 20. The camera module 21 may receive a target image of the analyte solution, and the smart device 20 displays the target image, along with a suggested target position icon on the target image.

A user may hold the smart device 20 along with the detecting device 10 on it toward the analyte solution in a toilet bowl. The user may further point the first light beam L1 to the analyte solution, so that the light detection module 16 receives the second light beam L2, which has passed through the analyte solution and been reflected by the inside surface of the toilet bowl. Therefore, the second light beam L2 will contain the absorption of the analyte solution. Preferably, a user should direct the first light beam L1 to a relatively shallow point in the toilet bowl.

When the user points the first light beam L1 to the analyte solution in the toilet bowl, the light beam can travel through the liquid with a better transmittance if the light beam is directed to a shallow position in the container without being blocked by suspended matter in the liquid, so that the light detection module 16 can receive a second light beam L2 with a higher intensity and obtain a more accurate test result. Furthermore, according to the shape of a toilet bowl, the better position to perform the test is a point closer to the front end of the toilet bowl, which is usually a shallower point in the toilet bowl. Therefore, when the smart device 20 receives the target image from the camera module 21, the smart device 20 further displays a suggested target position icon at the front end of the toilet bowl in the target image, providing the user with a suggested position to point the first light beam L1 thereto.

When the processor unit generates the positive or negative result information and the transmission unit transmits the result information to the smart device 20, the smart device 20 displays a positive or a negative result icon.

Figure 8A:
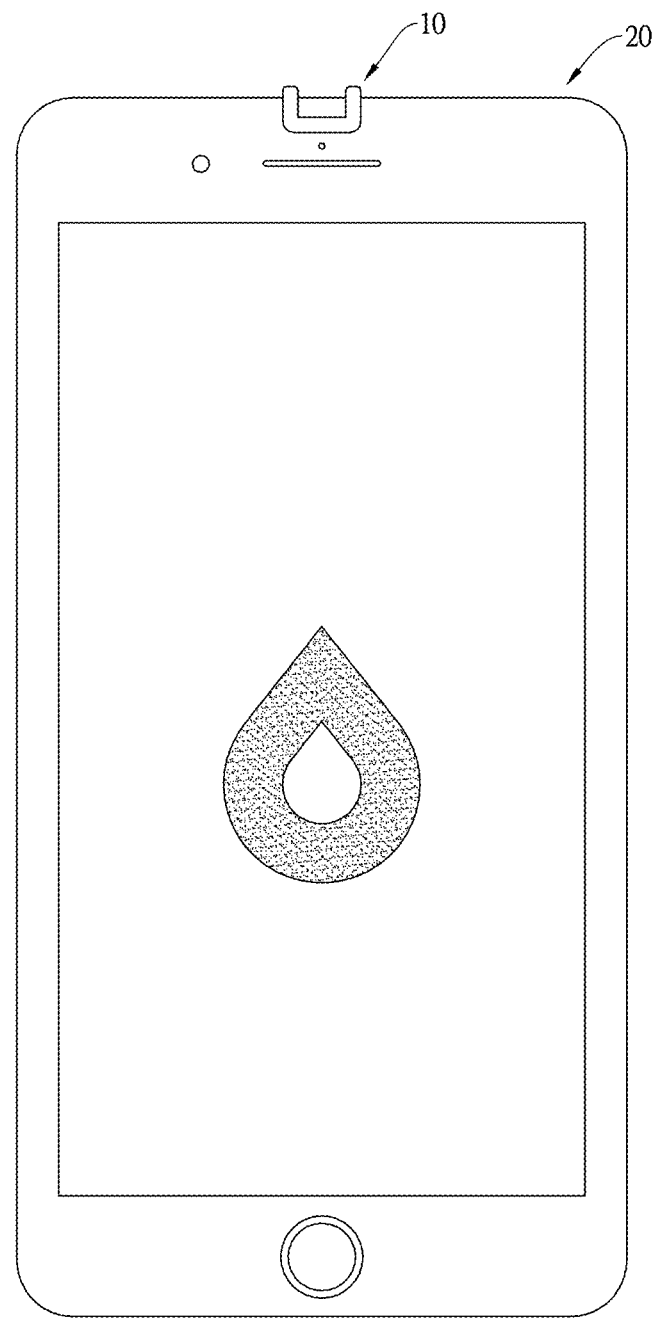
FIG. 8A and FIG. 8B are operational schematic views of the hemoglobin detecting device of the present invention.
Figure 8B:
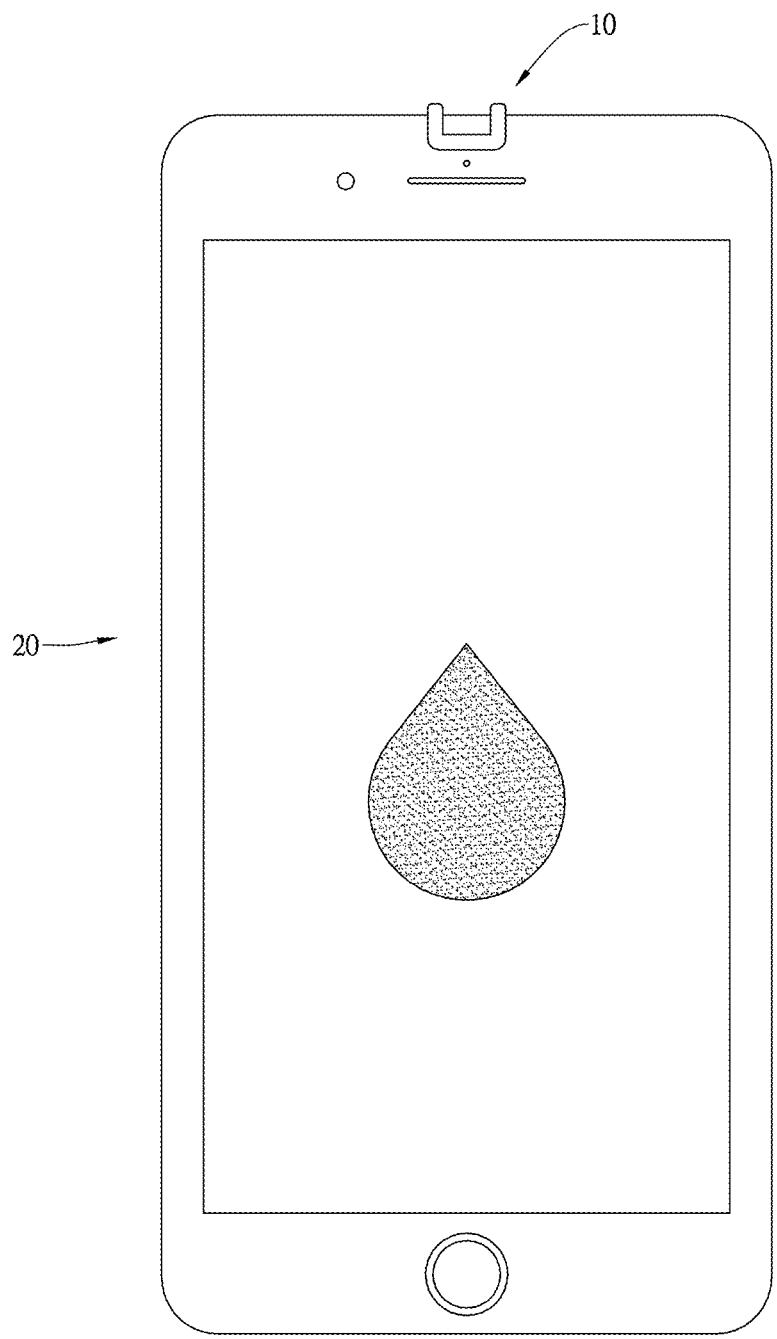

For example, with reference to FIG. 8A, when the processor unit 13 generates a negative result information, the smart device 20 displays an icon of a hollow blood drop figure, indicating that the analyte solution does not contain any blood or hemoglobin. With reference to FIG. 8B, when the processor unit 13 generates a positive result information, the smart device 20 displays an icon of a solid blood drop figure, indicating that the analyte solution does contain blood or hemoglobin. The result icons provide an easy and comprehensible indication of the test results for the user.

With reference to FIG. 1, in a sixth embodiment of the present invention, the hemoglobin detecting device 10 further includes a concentrator component 18. The concentrator component 18 is mounted inside the shell component 11 according to the position of the light source 15. In the embodiment, the concentrator component 18 is a condenser (focus) lens. The concentrator component 18 concentrates the first light beam L1 to form a narrow and condensed first light beam L1 with higher intensity, thus improving the detecting result.

The following embodiments describe the detailed method to determine whether the absorption spectrum of the analyte solution matches a target spectrum.

In a seventh embodiment of the present invention, the second light beam L2 includes a first wavelength light, a second wavelength light, a third wavelength light, and a fourth wavelength light. The light detection module 16 receives the second light beam L2, and generates a light intensity information. The light intensity information includes a first intensity signal S1 relating to the first wavelength light, a second intensity signal S2 relating to the second wavelength light, a third intensity signal S3 relating to the third wavelength light, and a fourth intensity signal S4 relating to the fourth wavelength light. A wavelength of the first wavelength light is smaller than a wavelength of the second wavelength light, the wavelength of the second wavelength light is smaller than a wavelength of the third wavelength light, and the wavelength of the third wavelength light is smaller than a wavelength of the fourth wavelength light.

Furthermore, the processor unit 13 receives the light intensity information from the light detection module 16, and determines whether the absorption spectrum of the analyte solution matches a target spectrum. The spectrum of the analyte solution matches the target spectrum if:

the second intensity signal S2, the third intensity signal S3 and the fourth intensity signal S4 are larger than the first intensity signal S1; and the second intensity signal S2 and the fourth intensity signal S4 are larger than the third intensity signal S3.

When the absorption spectrum of the analyte solution matches the target spectrum, the processor unit 13 generates a positive result information; when the absorption spectrum of the analyte solution does not match the target spectrum, the processor unit 13 generates a negative result information.

Figure 9:
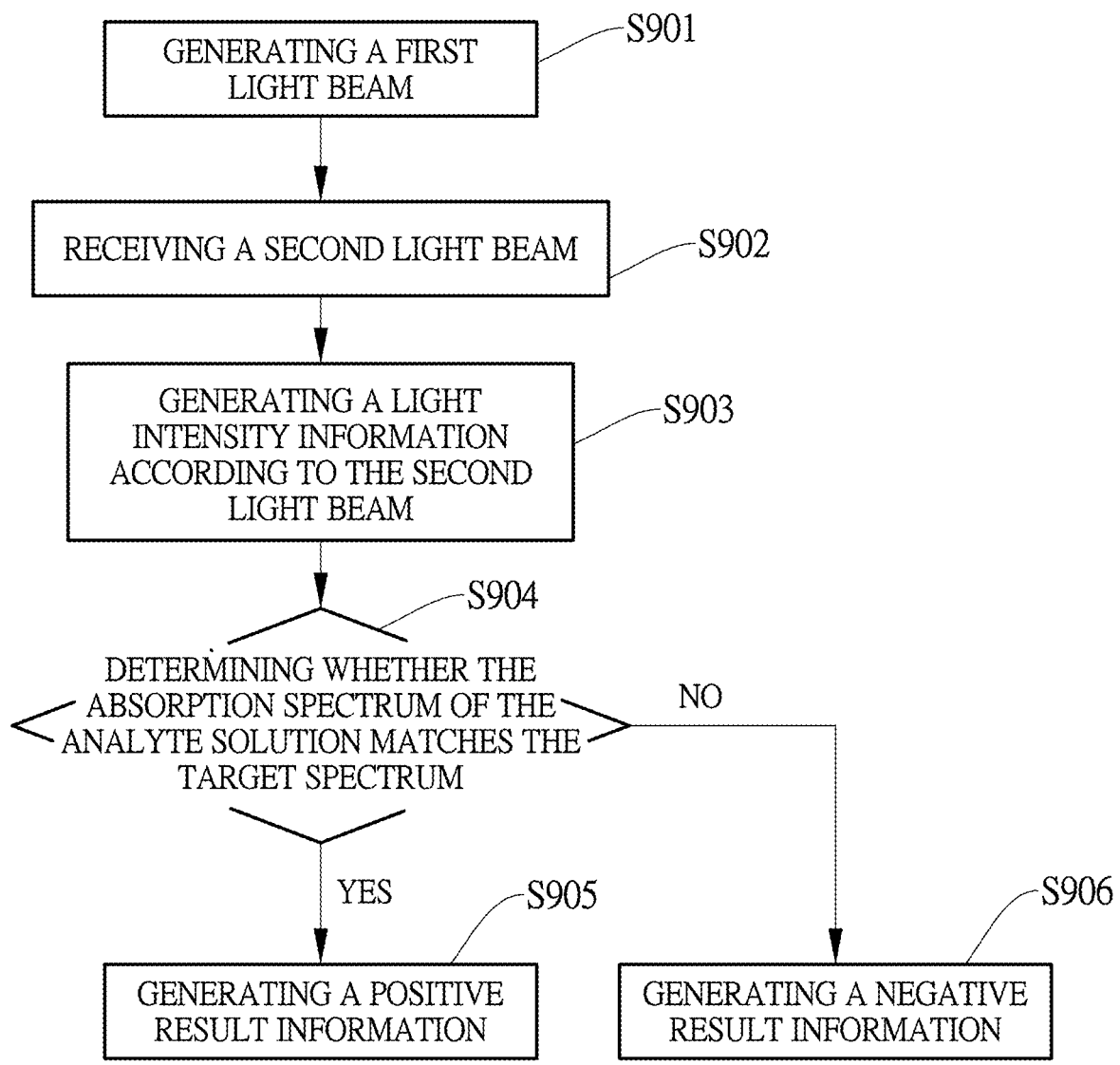
FIG. 9 is a flow chart of a seventh embodiment of the hemoglobin detecting device of the present invention.

With reference to FIG. 9, the present invention provides a hemoglobin detecting method, including the following steps:

generating a first light beam L1 (S901);

receiving a second light beam L2, which is formed by the first light beam L1 passing through the analyte solution and being reflected (S902)

generating a light intensity information (S903); wherein the light intensity information includes a first intensity signal S1 relating to the first wavelength light, a second intensity signal S2 relating to the second wavelength light, a third intensity signal S3 relating to the third wavelength light, and a fourth intensity signal S4 relating to the fourth wavelength light;

determining whether the absorption spectrum of the analyte solution matches the target spectrum according to the light intensity information (S904);

when the absorption spectrum of the analyte solution matches the target spectrum, generating a positive result information (S905);

when the absorption spectrum of the analyte solution does not match the target spectrum, generating a negative result information (S906); wherein the spectrum of the analyte solution matches the target spectrum if:

the second intensity signal S2, the third intensity signal S3 and the fourth intensity signal S4 are larger than the first intensity signal S1; and the second intensity signal S2 and the fourth intensity signal S4 are larger than the third intensity signal S3.

In an embodiment of the present invention, the wavelength of the first wavelength light is 500 nm, the wavelength of the second wavelength light is 541 nm, the wavelength of the third wavelength light is 550 nm, and the wavelength of the fourth wavelength light is 577 nm.

Figure 10:
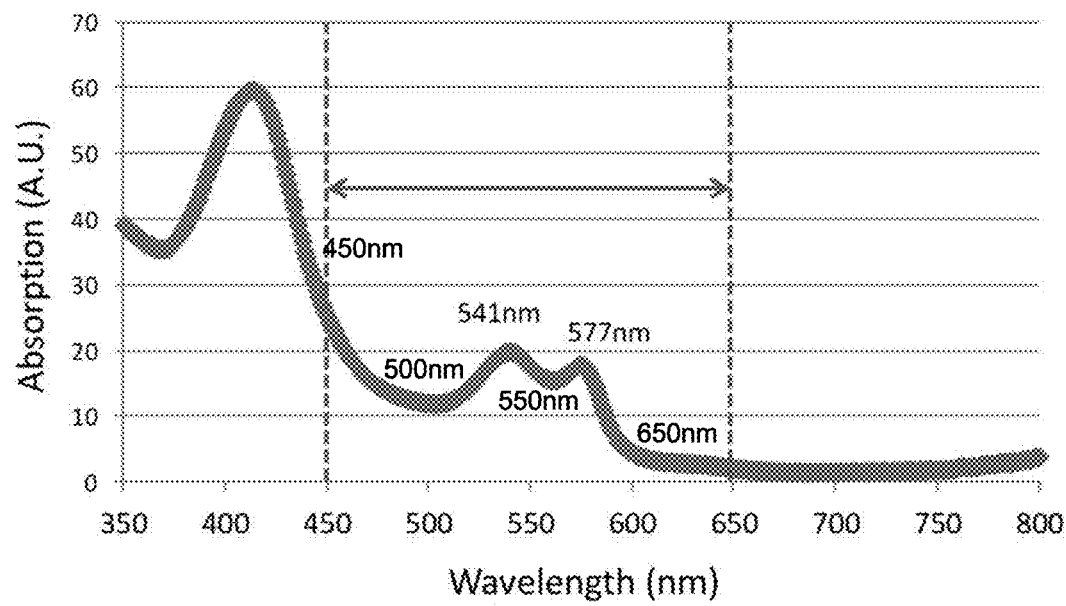
FIG. 10 is an absorption spectrum graph of a target spectrum of the hemoglobin detecting device of the present invention.

FIG. 10 shows an absorption spectrum of a blood solution and also the target spectrum of the present invention. The light source 15 may be an LED light source in the present invention. The LED light source may generate a light beam that covers most of the visible light frequency bandwidths, which include wavelengths ranging from 450 nm to 650 nm. Therefore, in the present embodiment, the determination is made according to the bandwidth of the first light beam L1 and the feature of the target spectrum. The light detection module 16 detects the intensity signals corresponding to the wavelengths of 500 nm, 541 nm, 550 nm and 577 nm, which are feature points in the target spectrum, so that the processor unit 13 can determine whether the absorption spectrum of the analyte solution matches the target spectrum.

According to the target spectrum shown in FIG. 10, it is apparent that within the absorption spectrum of a blood solution, the intensity of light with wavelengths of 541 nm and 577 nm is higher than the intensity of light with wavelength of 550 nm, while the intensity of light with wavelengths of 541 nm, 550 nm, and 577 nm is higher than the intensity of light with wavelength of 500 nm. Therefore, the processor unit 13 determines whether the absorption spectrum of the analyte solution matches the target spectrum according to the first, the second, the third, and the fourth intensity signals S1-S4 that correspond to those feature points.

Figure 11:
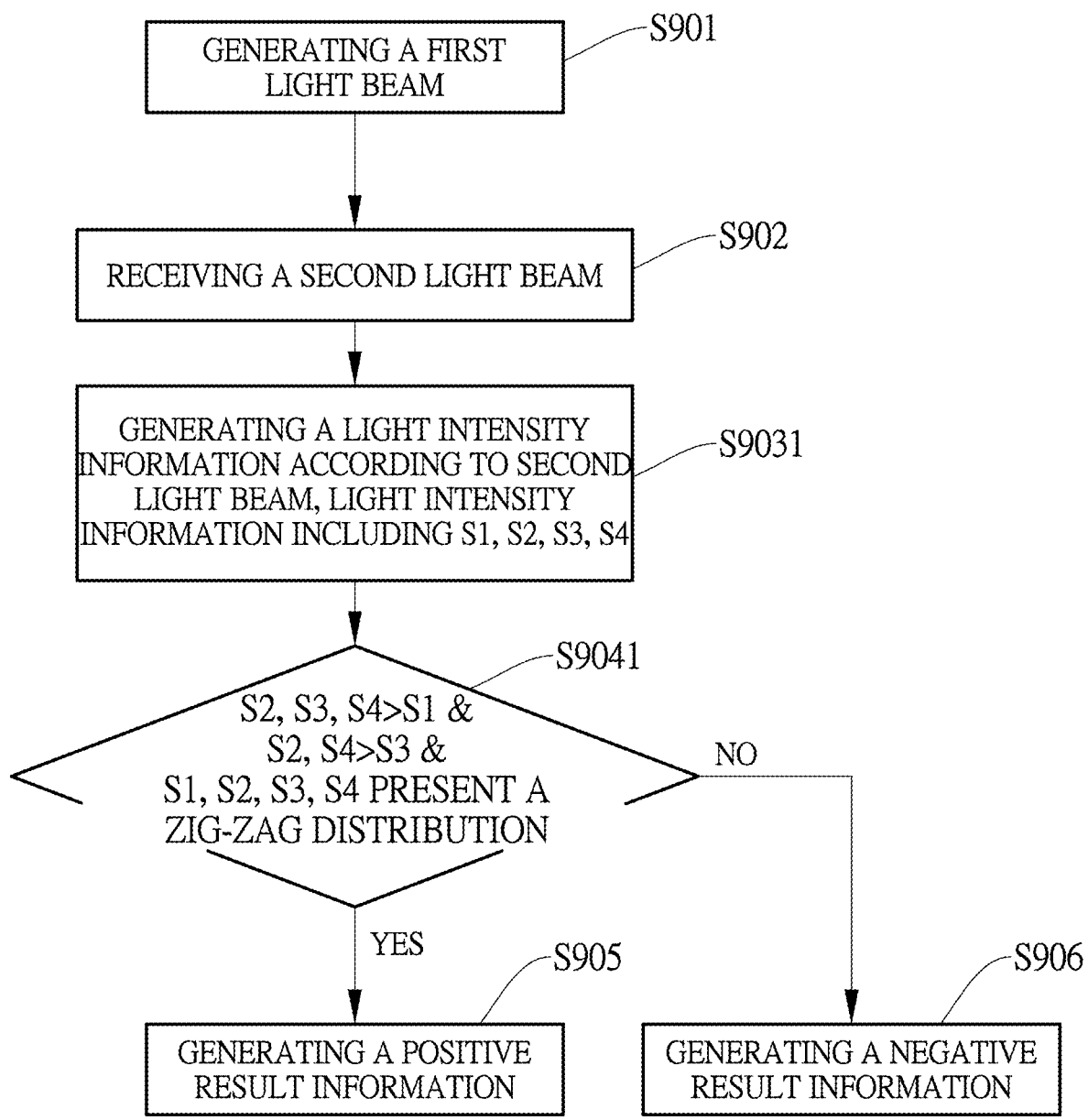
FIG. 11 is a flow chart of an eighth embodiment of the hemoglobin detecting method of the present invention.

With reference to FIG. 11, in an eighth embodiment of the present invention, when the processor unit 13 determines whether the absorption spectrum of the analyte solution matches the target spectrum, the processor unit 13 further determines if the first intensity signal S1, the second intensity signal S2, the third intensity signal S3, and the fourth intensity signal S4 present a zig-zag distribution (S9041). Furthermore, the processor unit 13 determines the absorption spectrum of the analyte solution matches the target spectrum (S905) only if:

the second intensity signal S2, the third intensity signal S3 and the fourth intensity signal S4 are larger than the first intensity signal S1;

the second intensity signal S2 and the fourth intensity signal S4 are larger than the third intensity signal S3; and the first intensity signal S1, the second intensity signal S2, the third intensity signal S3 and the fourth intensity signal S4 present a zig-zag distribution.

In the eighth embodiment, the processor unit further determines whether the first intensity signal S1, the second intensity signal S2, the third intensity signal S3 and the fourth intensity signal S4 should present a zig-zag distribution, which is another feature of the target spectrum. With such further condition, the accuracy of the detection is improved.

Figure 12:
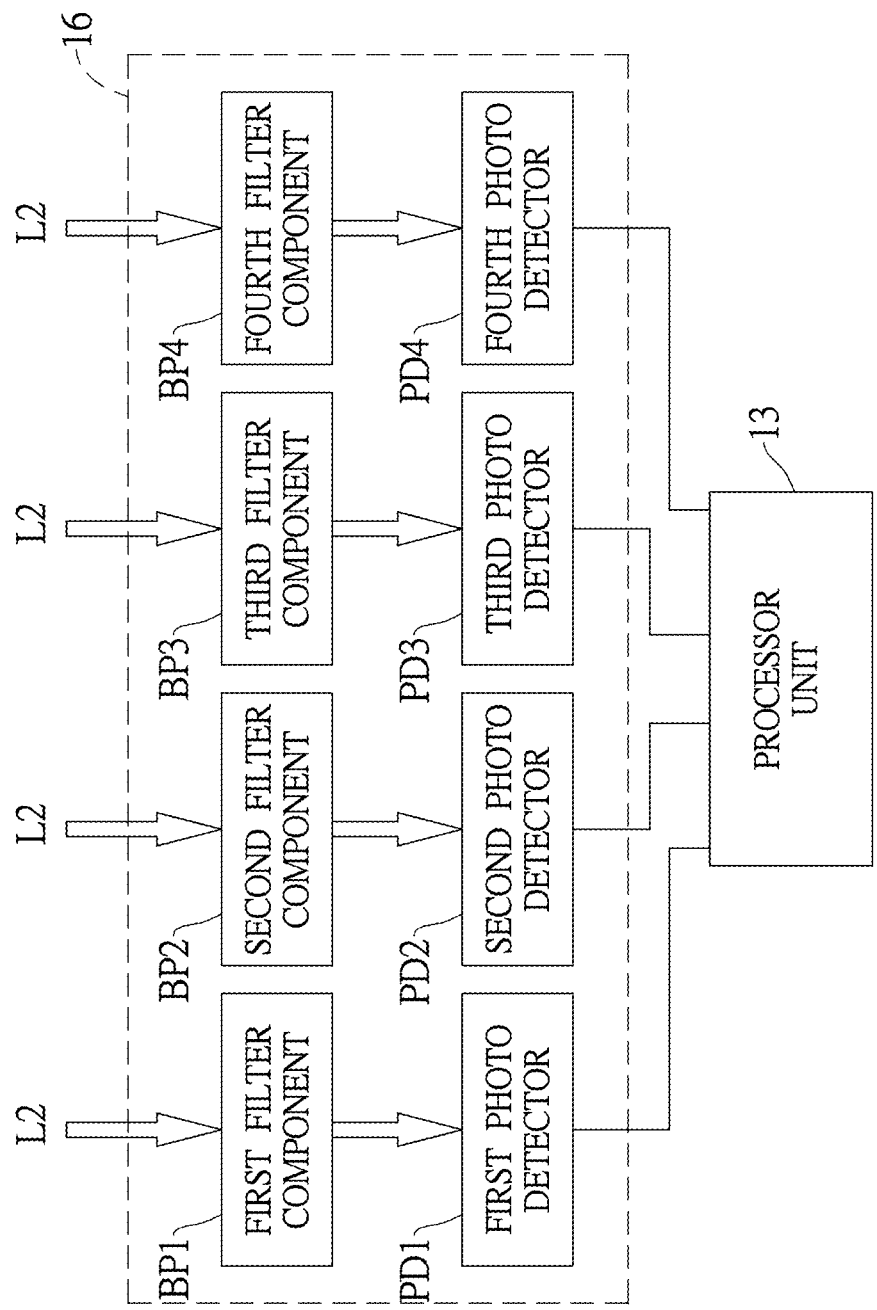
FIG. 12 is a block diagram of the light detection module of the seventh embodiment of the hemoglobin detecting device of the present invention.

With reference to FIG. 12, in the present embodiment, the light detection module 16 includes a first filter component BP1, a second filter component BP2, a third filter component BP3, and a fourth filter component BP4. The light detection module 16 further includes a first photo detector PD1, a second photo detector PD2, a third photo detector PD3, and a fourth photo detector PD4. The first photo detector PD1 receives the first wavelength light through the first filter component BP1; the second photo detector PD2 receives the second wavelength light through the second filter component BP2; the third photo detector PD3 receives the third wavelength light through the third filter component BP3; the fourth photo detector PD4 receives the fourth wavelength light through the fourth filter component BP4. In the present embodiment, the first filter component BP1 is a 500 nm wavelength bandpass filter, the second filter component BP2 is a 541 nm wavelength bandpass filter, the third filter component BP3 is a 550 nm wavelength bandpass filter, and the fourth filter component BP4 is a 571 nm wavelength bandpass filter. Therefore, when the second light beam L2 arrives at the light detection module 16, the first photo detector PD1, the second photo detector PD2, the third photo detector PD3, and the fourth photo detector PD4 receive the first wavelength light, the second wavelength light, the third wavelength light, and the fourth wavelength light, respectively, through the first filter component BP1, the second filter component BP2, the third filter component BP3, and the fourth filter component BP4, respectively, thus generating the first intensity signal S1, the second intensity signal S2, the third intensity signal S3, and the fourth intensity signal S4, respectively.

In a ninth embodiment of the present invention, the light intensity information generated by the light detection module 16 further includes a fifth intensity signal S5 relating to a fifth wavelength light and a sixth intensity signal S6 relating to a sixth wavelength light. A wavelength of the fifth wavelength light is shorter than the wavelength of the first wavelength light, and the wavelength of the sixth wavelength light is longer than the wavelength of the fourth wavelength light.

In the present embodiment, when the processor unit 13 determines whether the absorption spectrum of the analyte solution matches the target spectrum according to the light intensity information, the processor unit 13 further determines whether the fifth intensity signal S5 is larger than the first intensity signal S1. Furthermore, the processor unit 13 determines that the spectrum of the analyte solution matches the target spectrum when the light intensity information also meets the following condition: the fifth intensity signal S5, the first intensity signal S1, the second intensity signal S2, the third intensity signal S3, and the fourth intensity signal S4 are larger than the sixth intensity signal S6 (S3042).

Figure 13:
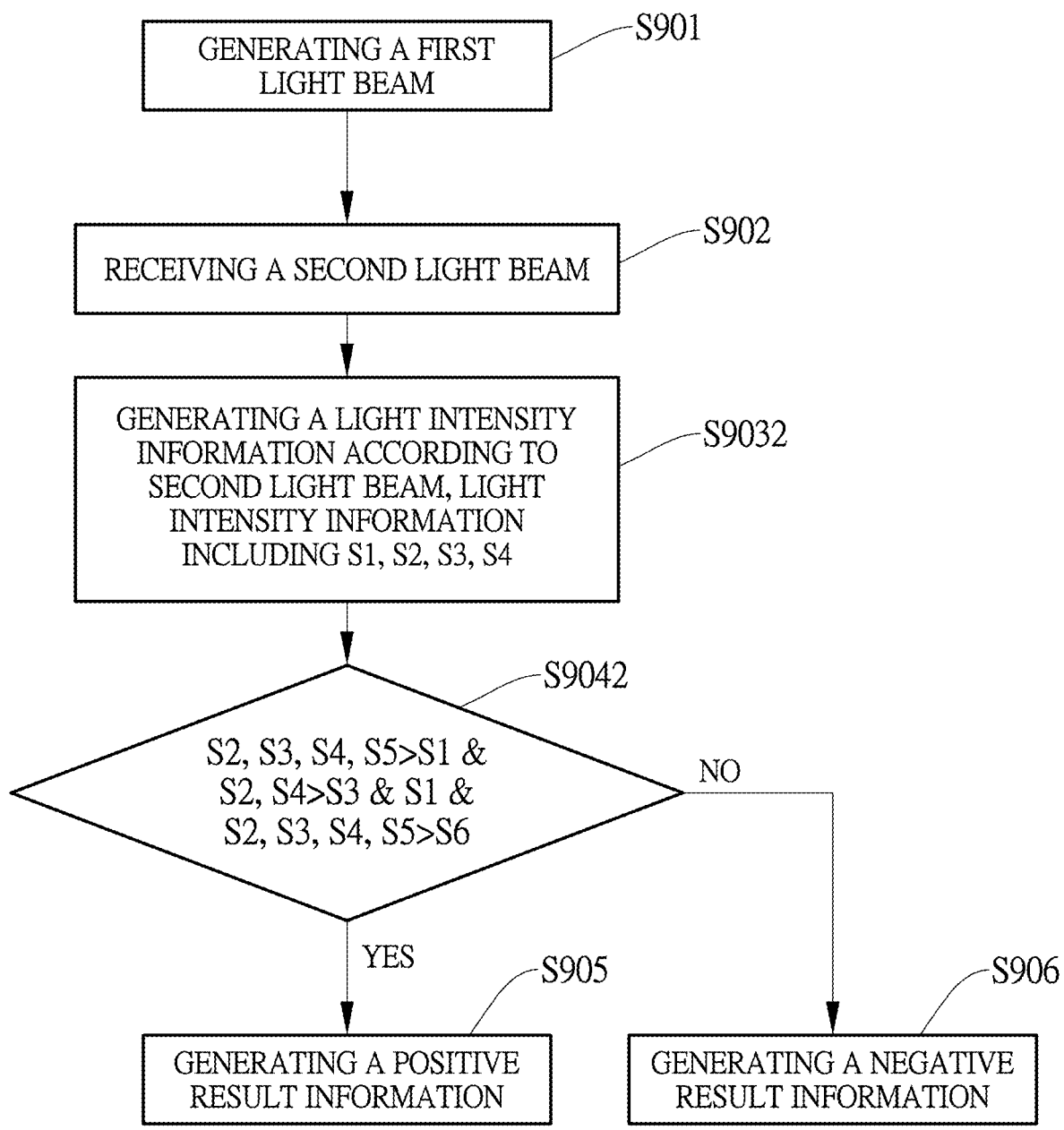
FIG. 13 is a flow chart of a ninth embodiment of the hemoglobin detecting method of the present invention.

With reference to FIG. 13, to be more specific, in the step of determining whether the absorption spectrum of the analyte solution matches the target spectrum according to the light intensity information (S904), the absorption spectrum of the analyte solution matches the target spectrum if:
the second intensity signal S2, the third intensity signal S3, the fourth intensity signal S4 and the fifth intensity signal S5 are larger than the first intensity signal S1; and
the second intensity signal S2 and the fourth intensity signal S4 are larger than the third intensity signal S3; and
the first intensity signal S1, the second intensity signal S2, the third intensity signal S3, the fourth intensity signal S4 and the fifth intensity signal S5 are larger than the sixth intensity signal S6.

In an embodiment of the present invention, the wavelength of the fifth wavelength light is 450 nm, and the wavelength of the sixth wavelength light is 600 nm.

Therefore, in the present embodiment, the light detection module 16 further generates the fifth intensity signal S5 relating to the 450 nm wavelength and the sixth intensity signal S6 relating to the 600 nm wavelength light in the second light beam L2. The light detection module 16 collects two more intensity signals relating to two more feature points in the target spectrum, so that the processor unit 13 has more detailed conditions to determine whether to generate a positive result information, thus improving the accuracy of the processor unit 13.

Figure 14:
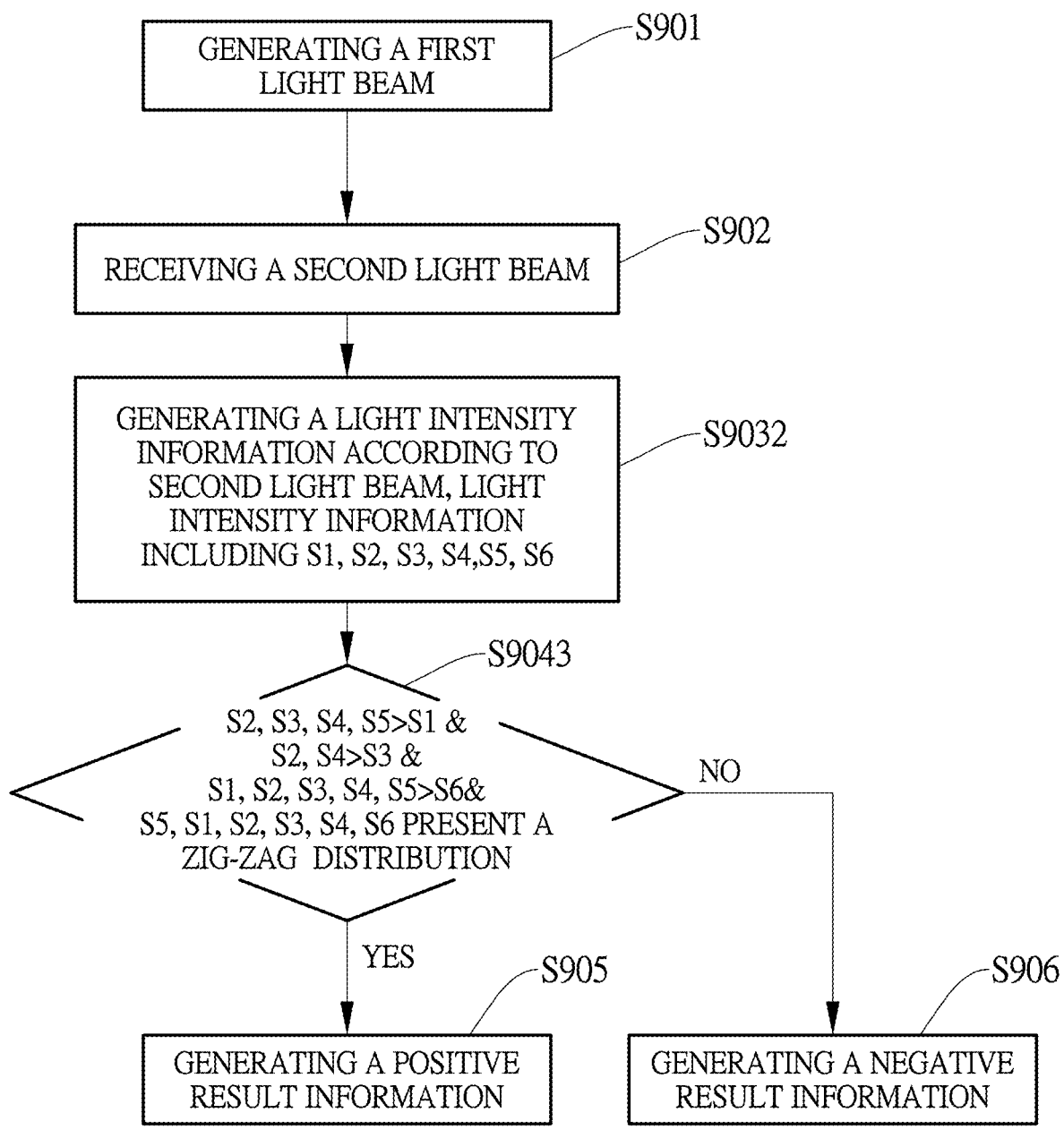
FIG. 14 is a flow chart of a tenth embodiment of the hemoglobin detecting method of the present invention.

With reference to FIG. 14, in a tenth embodiment of the present invention, when the processor unit 13 determines whether the absorption spectrum of the analyte solution matches the target spectrum, the processor further determines if the fifth intensity signal S5, the first intensity signal S1, the second intensity signal S2, the third intensity signal S3, the fourth intensity signal S4 and the sixth intensity signal S6 present a zig-zag distribution (S9043). The processor unit 13 determines the absorption spectrum of the analyte solution matches the target spectrum (S905) only if:
the second intensity signal S2, the third intensity signal S3, the fourth intensity signal S4 and the fifth intensity signal S5 are larger than the first intensity signal S1;
the second intensity signal S2 and the fourth intensity signal S4 are larger than the third intensity signal S3;
the first intensity signal S1, the second intensity signal S2, the third intensity signal S3, the fourth intensity signal S4 and the fifth intensity signal S5 are larger than the sixth intensity signal S6; and
the fifth intensity signal S5, the first intensity signal S1, the second intensity signal S2, the third intensity signal S3, the fourth intensity signal S4 and the sixth intensity signal S6 present a zig-zag distribution.

Figure 15:
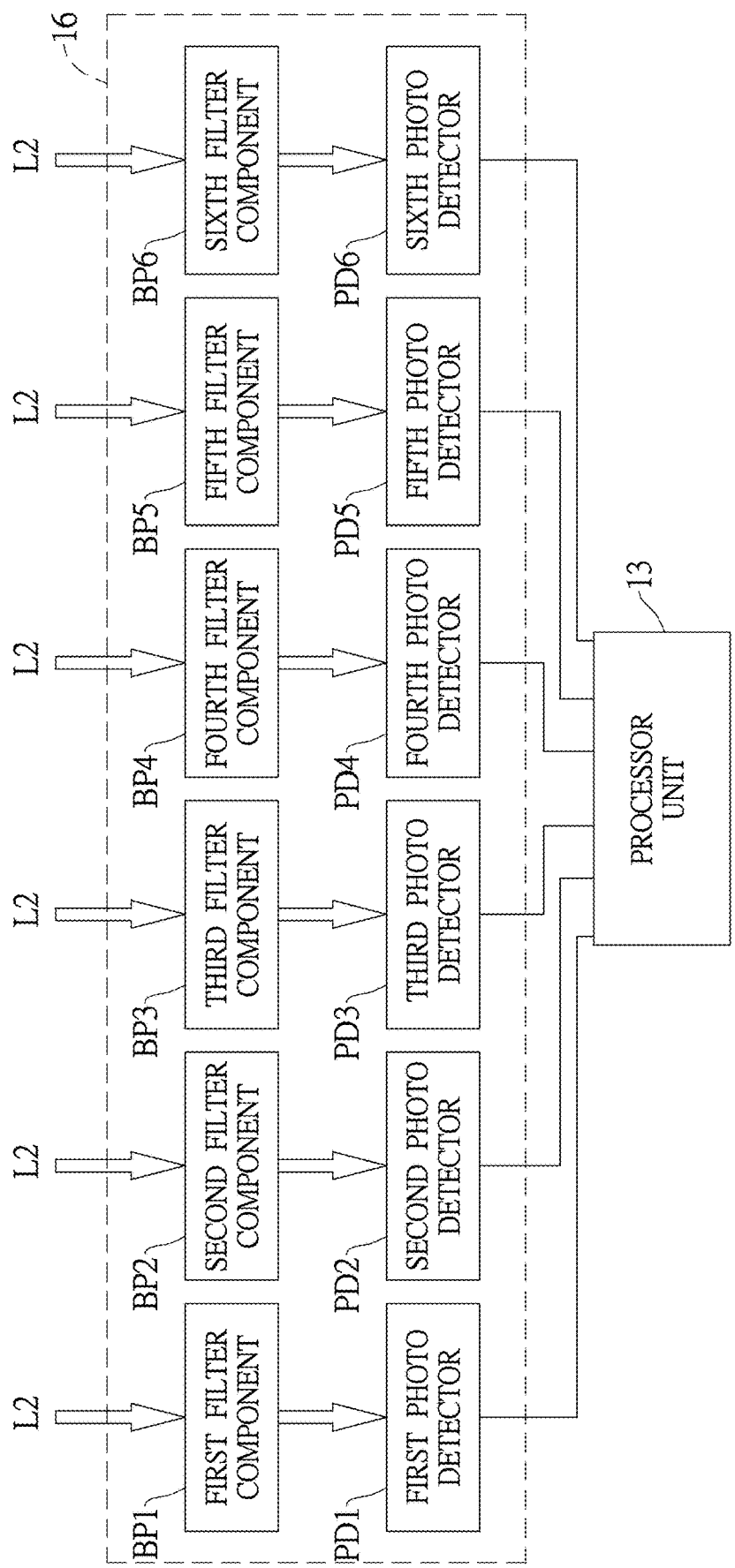
FIG. 15 is a block diagram of the light detection module of the ninth embodiment of the hemoglobin detecting device of the present invention.

With reference to FIG. 15 in the present embodiment, in order to obtain the first to the sixth intensity signals S6, the light detection module 16 further includes a fifth filter component BP5, a sixth filter component BP6, a fifth photo detector PD5, and a sixth photo detector PD6. The fifth photo detector PD5 receives the fifth wavelength light through the fifth filter component BP5. The sixth photo detector PD6 receives the sixth wavelength light through the sixth filter component BP6. Furthermore, the fifth filter component BP5 is a 450 nm bandpass filter, and the sixth filter component BP6 is a 600 nm bandpass filter. Therefore, the second light beam L2 is filtered to form the fifth wavelength light and the sixth wavelength light, so that the fifth photo detector PD5 and the sixth photo detector PD6 generate the fifth intensity signal S5 and the sixth intensity signal S6 respectively.

In the present embodiment, the light detection module 16 further collects the fifth wavelength light with wavelength of 450 nm and the sixth wavelength light with wavelength of 600 nm, generating six light intensity signals in total. The two additional feature points according to the target spectrum further improve the accuracy of the test results.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:
1. A hemoglobin detecting device, comprising:
a shell component;
a fixing part, connected with the shell component, wherein the fixing part enables the shell component to be engaged with a smart device;
a processor unit, mounted inside the shell component;
a transmission unit, mounted inside the shell component and electrically connected to the processor unit;
a light source, mounted inside the shell component and electrically connected to the processor unit, wherein the light source generates a first light beam;
a light detection module, mounted inside the shell component and electrically connected to the processor unit; wherein
the light detection module receives a second light beam and generates a light intensity information according to the second light beam, wherein the first light beam passes through an analyte solution and is reflected to form the second light beam;
the second light beam includes a first wavelength light, a second wavelength light, a third wavelength light, and a fourth wavelength light, wherein a wavelength of the first wavelength light is smaller than a wavelength of the second wavelength light, the wavelength of the second wavelength light is smaller than a wavelength of the third wavelength light, and the wavelength of the third wavelength light is smaller than a wavelength of the fourth wavelength light;
the light intensity information includes a first intensity signal relating to the first wavelength light, a second intensity signal relating to the second wavelength light, a third intensity signal relating to the third wavelength light, and a fourth intensity signal relating to the fourth wavelength light;

the processor unit receives the light intensity information from the light detection module, and determines whether an absorption spectrum of the analyte solution matches a target spectrum;

the absorption spectrum of the analyte solution matches the target spectrum if:
  the second intensity signal, the third intensity signal and the fourth intensity signal are larger than the first intensity signal; and
  the second intensity signal and the fourth intensity signal are larger than the third intensity signal;

when the absorption spectrum of the analyte solution matches the target spectrum, the processor unit generates a positive result information;

when the absorption spectrum of the analyte solution does not match the target spectrum, the processor unit generates a negative result information; wherein the transmission unit receives the positive result information or the negative result information from the processor unit, and transmits the positive result information or the negative result information to the smart device.

2. The hemoglobin detecting device as claimed in claim 1, wherein the fixing part is connected with the shell component to form a C-shaped structure, and a width of a hollow part of the C-shaped structure fits a thickness or a width of the smart device.

3. The hemoglobin detecting device as claimed in claim 1, wherein the fixing part is a clamping component.

4. The hemoglobin detecting device as claimed in claim 1, wherein the transmission unit is wirelessly connected to the smart device.

5. The hemoglobin detecting device as claimed in claim 1, wherein the light source begins to generate the first light beam, and the light detection module begins to receive the second light beam when the processor unit receives a first signal from the smart device through the transmission unit.

6. The hemoglobin detecting device as claimed in claim 1, further comprising:
  a power unit, electrically connected to the processor unit, the transmission unit, the light source, and the light detection module.

7. The hemoglobin detecting device as claimed in claim 1, wherein the processor unit further determines whether the first intensity signal, the second intensity signal, the third intensity signal, and the fourth intensity signal present a zig-zag distribution;
  wherein the absorption spectrum of the analyte solution matches the target spectrum if:
    the second intensity signal, the third intensity signal, and the fourth intensity signal are larger than the first intensity signal;
    the second intensity signal and the fourth intensity signal are larger than the third intensity signal; and
    the first intensity signal, the second intensity signal, the third intensity signal and the fourth intensity signal present a zig-zag distribution.

8. The hemoglobin detecting device as claimed in claim 1, wherein the wavelength of the first wavelength light is 500 nm, the wavelength of the second wavelength light is 541 nm, the wavelength of the third wavelength light is 550 nm, and the wavelength of the fourth wavelength light is 577 nm.

9. The hemoglobin detecting device as claimed in claim 1, wherein the light detection module comprises:

a first filter component;
a first photo detector, receiving the first wavelength light through the first filter component, and generating the first intensity signal according to the first wavelength light;
a second filter component;
a second photo detector, receiving the second wavelength light through the second filter component, and generating the second intensity signal according to the second wavelength light;
a third filter component;
a third photo detector, receiving the third wavelength light through the third filter component, and generating the third intensity signal according to the third wavelength light;
a fourth filter component;
a fourth photo detector, receiving the fourth wavelength light through the fourth filter component, and generating the fourth intensity signal according to the fourth wavelength light.

10. The hemoglobin detecting device as claimed in claim 1, further comprising:
  a concentrator component, mounted inside the shell component according to the position of the light source, wherein the first light beam of the light source runs through the concentrator component.

11. The hemoglobin detecting device as claimed in claim 1, wherein the transmission unit is a connector.

12. The hemoglobin detecting device as claimed in claim 6, wherein the power unit comprises a connecting port; wherein
  the connecting port is to connect with a power supply module to receive an input power, and the power unit transmits the input power to the processor unit, the transmission unit, the light source, and the light detection module.

13. The hemoglobin detecting device as claimed in claim 1, wherein the light intensity information further includes a fifth intensity signal relating to a fifth wavelength light, and a sixth intensity signal relating to a sixth wavelength light; wherein a wavelength of the fifth wavelength light is smaller than the wavelength of the first wavelength light, and a wavelength of the sixth wavelength light is larger than the wavelength of the fourth wavelength light;
  wherein the processor unit further determines whether the fifth intensity signal is larger than the first intensity signal, and whether the fifth intensity signal, the first intensity signal, the second intensity signal, the third intensity signal, and the fourth intensity signal are larger than the sixth intensity signal;
  wherein the absorption spectrum of the analyte solution matches the target spectrum if:
    the fifth intensity signal, the second intensity signal, the third intensity signal, and the fourth intensity are larger than the first intensity signal;
    the second intensity signal and the fourth intensity are larger than the third intensity signal; and
    the fifth intensity signal, the first intensity signal, the second intensity signal, the third intensity signal, and the fourth intensity signal are larger than the sixth intensity signal.

14. The hemoglobin detecting device as claimed in claim 13, wherein the processor unit further determines whether the fifth intensity signal, the first intensity signal, the second intensity signal, the third intensity signal, the fourth intensity signal, and the sixth intensity signal present a zig-zag distribution;

wherein the absorption spectrum of the analyte solution matches the target spectrum if:
the fifth intensity signal, the second intensity signal, the third intensity signal, and the fourth intensity are larger than the first intensity signal;
the second intensity signal and the fourth intensity are larger than the third intensity signal;
the fifth intensity signal, the first intensity signal, the second intensity signal, the third intensity signal, and the fourth intensity signal are larger than the sixth intensity signal; and
the first intensity signal, the second intensity signal, the third intensity signal, the fourth intensity signal, and the sixth intensity signal present a zig-zag distribution.

15. The hemoglobin detecting device as claimed in claim 13, wherein the wavelength of the fifth wavelength light is 450 nm, and the wavelength of the sixth wavelength light is 600 nm.

16. The hemoglobin detecting device as claimed in claim 13, wherein the light detection module comprises:
a first filter component;
a first photo detector, receiving the first wavelength light through the first filter component, and generating the first intensity signal according to the first wavelength light;
a second filter component;
a second photo detector, receiving the second wavelength light through the second filter component, and generating the second intensity signal according to the second wavelength light;
a third filter component;
a third photo detector, receiving the third wavelength light through the third filter component, and generating the third intensity signal according to the third wavelength light;
a fourth filter component;
a fourth photo detector, receiving the fourth wavelength light through the fourth filter component, and generating the fourth intensity signal according to the fourth wavelength light;
a fifth filter component;
a fifth photo detector, receiving the fifth wavelength light through the fifth filter component, and generating the fifth intensity signal according to the fifth wavelength light;
a sixth filter component;
a sixth photo detector, receiving the sixth wavelength light through the sixth filter component, and generating the sixth intensity signal according to the sixth wavelength light.

* * * * *